Aug. 9, 1960 C. E. SULLIVAN Plant Pat. 1,963
WALNUT TREE
Filed March 13, 1959
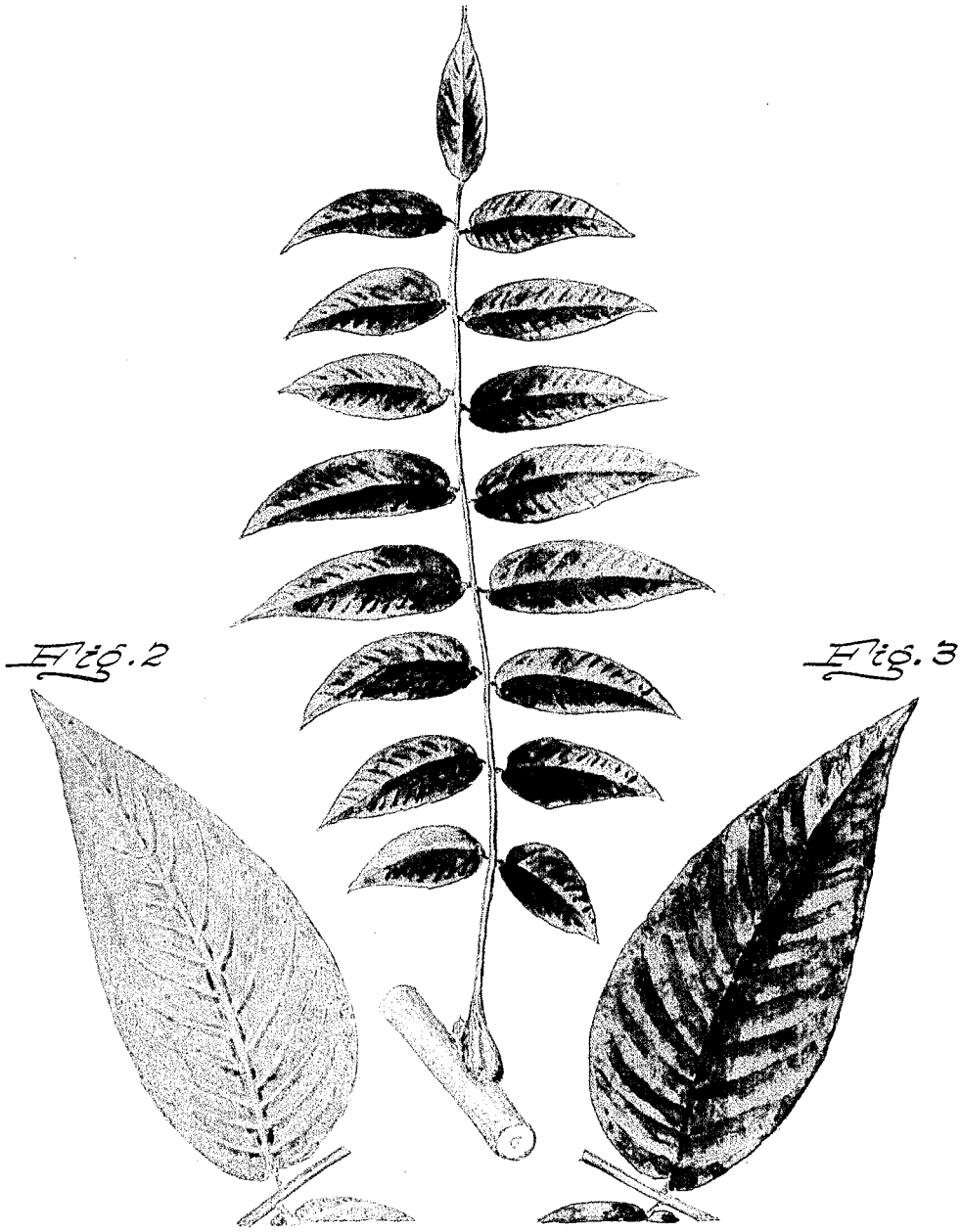
WITNESS
Addison E. Avery
INVENTOR
Charles Edward Sullivan
Webster & Webster
ATTYS.

United States Patent Office

Plant Pat. 1,963
Patented Aug. 9, 1960

1,963

WALNUT TREE

Charles Edward Sullivan, Garden Highway, Yuba City, Calif.

Filed Mar. 13, 1959, Ser. No. 799,394

1 Claim. (Cl. 47—62)

This discovery relates to a new and distinct variety of walnut tree especially adapted for use as a rootstock for all varieties of English walnuts. The present variety of walnut tree is particularly, and desirably, characterized by substantial vigor and relatively great resistance to oak root fungus, crown rot, root rot, and nematode infestation, together with wide tolerance to soil conditions; i.e., wet, dry, and heavy soil. As a result the variety provides an excellent rootstock which remains strong and healthy over a long period of years, and notwithstanding adverse growing conditions to which the variety may be subject, such as those mentioned above.

A further outstanding characteristic of the present variety is that it is capable—when used as a rootstock—of producing a grafted or budded English walnut tree which is commonly much larger—in any growing period—than the same English walnut implanted on the conventional black walnut rootstock (unpatented).

An additional important characteristic of the present variety is its ability to produce an implanted English walnut tree which will consistently bear a larger crop of commercially acceptable nuts than otherwise; this for the reason that the tree grows larger than on a conventional rootstock, thus bearing a proportionately larger crop.

The present variety of walnut tree was discovered by me in my orchard located near Yuba City, Sutter County, California, under the following circumstances:

A block of Franquette (unpatented) walnuts grafted, with the exception of one as hereinafter noted, on conventional (Northern California Black Walnut) rootstock were grown in such orchard, and with the passage of time all—save such one—of the trees within a certain area died of oak root fungus. Such one remaining tree in said area continued to thrive, growing strong and vigorous, with a heavy production of nuts. All this led me to the recognition that the rootstock of the tree which survived was a variety distinct from such conventional rootstock and that it was a seedling which I knew, after inspection, to have originated—as a Paradox Hybrid—from a black walnut as the seed parent and an unknown variety of English walnut as the pollen parent.

After this discovery I selected the rootstock of such one tree for experimentation and testing, and subsequent asexual reproduction of said rootstock—which is the present claimed variety—clearly established not only its remarkable resistance to oak root fungus, but also the additional advantageous characteristics hereinbefore described.

Asexual reproduction of the variety was undertaken—on my behalf—by the University of California, at Davis, California, by the trench-layering method. More particularly, scions of the variety were grafted on a black walnut rootstock and grown to a one year tree in a nursery. Such tree was then removed in toto from the soil and laid in a trench; the root system of such tree having been covered with soil but the rest of the tree initially remaining exposed in the trench. Thereafter leaf buds broke into growth, formed shoots, and as the latter grew the trench was gradually filled with soil, and so as to cover the lower portion of such shoots. Roots then developed from the base of the shoots. After developing sufficiently, such shoots — including the roots — were severed from the parent layered tree and grown in an orchard; all having reflected the desirable characteristics of the original tree, and ran true thereto in all respects, including when used as rootstock.

In the drawings:

Fig. 1 shows a leaf comprised of a plurality of leaflets attached to a rachis.

Fig. 2 is an enlarged bottom plan view of the blade of a leaflet; the slight irregularity of the margin being illustrated, but existent serrations being too minute for effective illustration and are thus omitted.

Fig. 3 is a top plan view of the blade of a leaflet as shown in Fig. 2.

As the primary novel characteristics of the instant variety are not visual, a leaf and blades of leaflets are shown in the drawings as an aid to the botanical identification of the variety.

Referring now more specifically to the botanical details of this new and distinct variety of walnut tree, the following is an outline description thereof; all major color plate identifications being by reference to Maerz and Paul Dictionary Color, except where common terms of color definition are employed.

Tree:

*Size.*—Large.

*Growing habit.*—Strong; vigorous; upright; tendency to large numbers of side branches.

*Form.*—Substantially round or spherical, but somewhat flat on top.

*Adaptability.*—Very adaptable to heavy, sandy, wet, dry, or poor soil.

*Productivity.*—Few or no nuts, as is common with a cross between a black walnut and an English walnut.

*Bark.*—Color of new shoots—olive green. Color of twigs—light green. Color of trunk—greenish brown, turning to light brown as the tree matures. Bark at first smooth similar to English walnut, but roughens as the tree matures. Bark of new shoots non-pubescent but smooth and shiny.

*Wood.*—Pith very loose and open, with webbed sections in the core. Sap wood solid and firm, almost white in color. Heart wood solid and firm, almost white in color. Lenticels—very small.

*Foliage.*—Lustrous.

*Disease resistance.*—Highly resistant to oak root fungus, crown rot, root rot, and nematode infestation.

*Buds.*—Plump; well matured; semi-oval, with blunt point. Color—tan. Pubescent.

Leaves: Average length—10″ to 12″. Average number—3 to 5 per twig.

Leaflets: Average number per leaf—9 to 15 or more.

*Margin.*—Slightly irregular, with minute spaced serrations.

*Petiole.*—Round; very short, almost non-existent or substantially sessil.

*Glands.*—None.

*Form.*—Elliptical, with pointed tip.

*Pubescence.*—None.

*Color.*—Blades of leaflets: Top side—medium green (22–L–11); under side—lighter green (21–L–7). Prominent ribs on under side of blades—light greenish yellow (18–I–1). Shoots—medium to light green (19–L–6) with olive brown streak (15–L–6) on top. Rachis—medium to light green (19–L–6).

*Leaf scars.*—Heart or wing-shaped about ½" long. Center portion sunken, with a raised lobe at each of the three corners.

The variety is known to have substantial resistance to oak root fungus because of the conditions existent in the area, in my orchard, where the discovery of the variety was made. More particularly, the parent tree—grafted with a Franquette walnut—was originally believed to be a black walnut (i.e. the rootstock), but after my discovery such parent tree was evidently a Paradox Hybrid. Such tree grew in an area of my orchard infested with oak root fungus. In time all of the walnut trees in such area, as well as certain peach trees therein, died of oak root fungus, saving and excepting such parent tree of the instant variety. The latter continued to grow strong, vigorous, and large in the midst of the oak root fungus infestation and bore heavy crops of nuts.

Further, as to the resistance of the present variety to crown rot and root rot, this is believed to stem from the fact that the variety, as apparently a Paradox Hybrid, has a resultant natural resistance to crown and root damage from excess water and wet or heavy soil.

As to nematode infestation, reproduction of the variety by the University of California at Davis, California, and in its experimental or test plot, has substantiated the fact that the variety—in comparison to some other Paradox Hybrids—has greater resistance to this type of infestation.

The following is claimed:

A new and distinct variety of walnut tree, as shown and described, characterized by vigorous, upright, and strong growth with a tendency to large numbers of side branches; the bearing of few flowers and nuts; lustrous medium green foliage; leaves averaging three to five per shoot and ten to twelve inches in length, with nine to fifteen or more leaflets; elliptical leaflets with pointed tips; leaflets whose petiole is very short, almost non-existent or substantially sessil; relatively greater resistance to oak root fungus, crown rot, root rot, and nematode infestation, together with wide tolerance to soil and moisture conditions; and—as a rootstock—the ability to produce an English walnut tree which is vigorous in growth, large in size, and highly productive.

No references cited.